United States Patent
Workman, Jr. et al.

(10) Patent No.: US 10,345,228 B2
(45) Date of Patent: Jul. 9, 2019

(54) DARK REFERENCE STANDARD AND MEASUREMENT THEREOF

(71) Applicant: WESTCO SCIENTIFIC INSTRUMENTS, INC., Brookfield, CT (US)

(72) Inventors: Jerome J. Workman, Jr., Marlborough, MA (US); John Glaberson, N Sandy Hook, CT (US)

(73) Assignee: PROCESS SENSORS CORPORATION, Milford, MA (US)

( * ) Notice: Subject to any disclaimer, the term of this patent is extended or adjusted under 35 U.S.C. 154(b) by 41 days.

(21) Appl. No.: 15/447,959

(22) Filed: Mar. 2, 2017

(65) Prior Publication Data

US 2017/0254742 A1 Sep. 7, 2017

Related U.S. Application Data

(60) Provisional application No. 62/302,478, filed on Mar. 2, 2016.

(51) Int. Cl.
*G01N 21/27* (2006.01)

(52) U.S. Cl.
CPC ......... *G01N 21/278* (2013.01); *G01N 21/274* (2013.01)

(58) Field of Classification Search
CPC .. G01N 21/278; G01N 21/274; G01N 21/276; G01N 21/4785; G01D 18/00
See application file for complete search history.

(56) References Cited

U.S. PATENT DOCUMENTS

| | | | | |
|---|---|---|---|---|
| 3,646,159 A * | 2/1972 | Miller | ..................... | C08L 59/02 524/341 |
| 4,095,105 A * | 6/1978 | Rosenthal | ............ | G01N 21/278 250/252.1 |
| 4,725,147 A * | 2/1988 | Stoddart | ............. | G01N 21/274 356/243.1 |
| 6,002,482 A * | 12/1999 | Rothfritz | ............. | A61B 5/0059 356/243.5 |
| 6,226,541 B1 * | 5/2001 | Eppstein | .............. | A61B 5/0059 356/243.1 |
| 6,271,920 B1 * | 8/2001 | Macfarlane | ............... | G01J 3/52 356/243.5 |
| 7,717,630 B1 * | 5/2010 | Wan | ....................... | G03B 17/00 396/448 |
| 2006/0285108 A1 * | 12/2006 | Morrisroe | ............. | F23C 99/003 356/316 |
| 2012/0200844 A1 * | 8/2012 | Wallin | ................. | G01N 21/276 356/51 |
| 2015/0142364 A1 * | 5/2015 | Workman | ............ | G01N 21/274 702/104 |

* cited by examiner

*Primary Examiner* — Michael P LaPage
(74) *Attorney, Agent, or Firm* — Thomas | Horstemeyer, LLP; N. Andrew Crain; Jason M. Perilla

(57) ABSTRACT

Various embodiments of a dark reference standard for an instrument are described. In one embodiment, the dark reference standard includes a sample cup and an arrangement of dark reference standard materials. The arrangement of dark reference standard materials can be embodied as a dark glass, such as a welding glass, and a polymer film such as a carbon black or carbon black master polymer film.

19 Claims, 7 Drawing Sheets

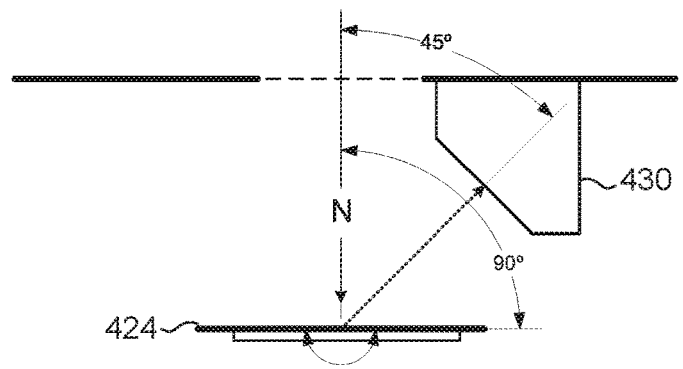
FIG. 5A  0°/45°
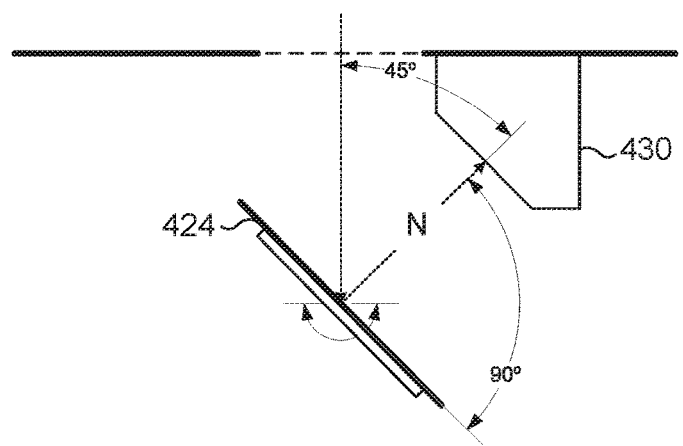
FIG. 5B  45°/0°
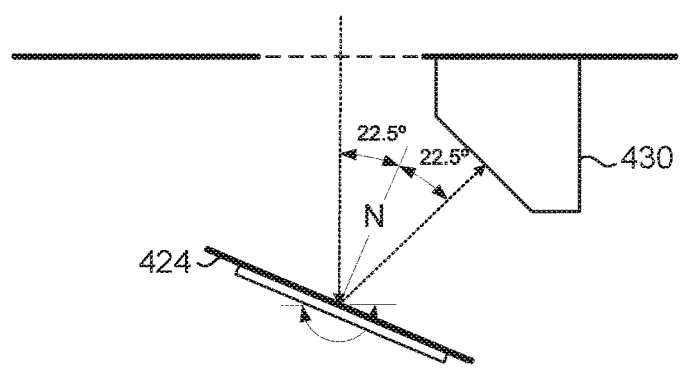
FIG. 5C  22.5°/22.5°

DARK REFERENCE STANDARD AND MEASUREMENT THEREOF

CROSS-REFERENCE TO RELATED APPLICATIONS

This application claims the benefit of U.S. Provisional Application No. 62/302,478, filed Mar. 2, 2016, the entire contents of which is hereby incorporated herein by reference.

BACKGROUND

The manner in which light (e.g., visible, near-ultraviolet, and near-infrared electromagnetic radiation) interacts with matter provides important information about the composition of the matter. Information on chemical substances, for example, can be determined from their specific absorption or emission of light. Thus, certain analytical procedures include an analysis of the amount of light absorbed or transmitted as that light passes through a sample. In that context, spectrophotometry is the quantitative measurement of the reflection and transmission of light through/from matter as a function of wavelength. Spectrophotometry is a more particular term than electromagnetic spectroscopy in that spectrophotometry deals with visible light, near-ultraviolet, and near-infrared, but generally does not include time-resolved spectroscopic techniques.

Spectrophotometers are relied upon across various technical and scientific fields, such as physics, materials science, chemistry, biology, and biochemistry. Spectrophotometers are also used in various industries including the semiconductor, laser manufacturing, optical manufacturing, printing, and forensic examination industries. When properly calibrated, a spectrophotometer can be used to determine what substances are present in a composition under test through the observed wavelengths of transmittance or reflectance, converted to absorbance for quantitative measurements.

BRIEF DESCRIPTION OF THE DRAWINGS

For a more complete understanding of the embodiments and the advantages thereof, reference is now made to the following description, in conjunction with the accompanying figures briefly described as follows:

FIG. 5A-5C illustrate an example geometries of detectors and sampling trays of the example monochromator of FIG. 4 according to an embodiment described herein.

Figure 1:
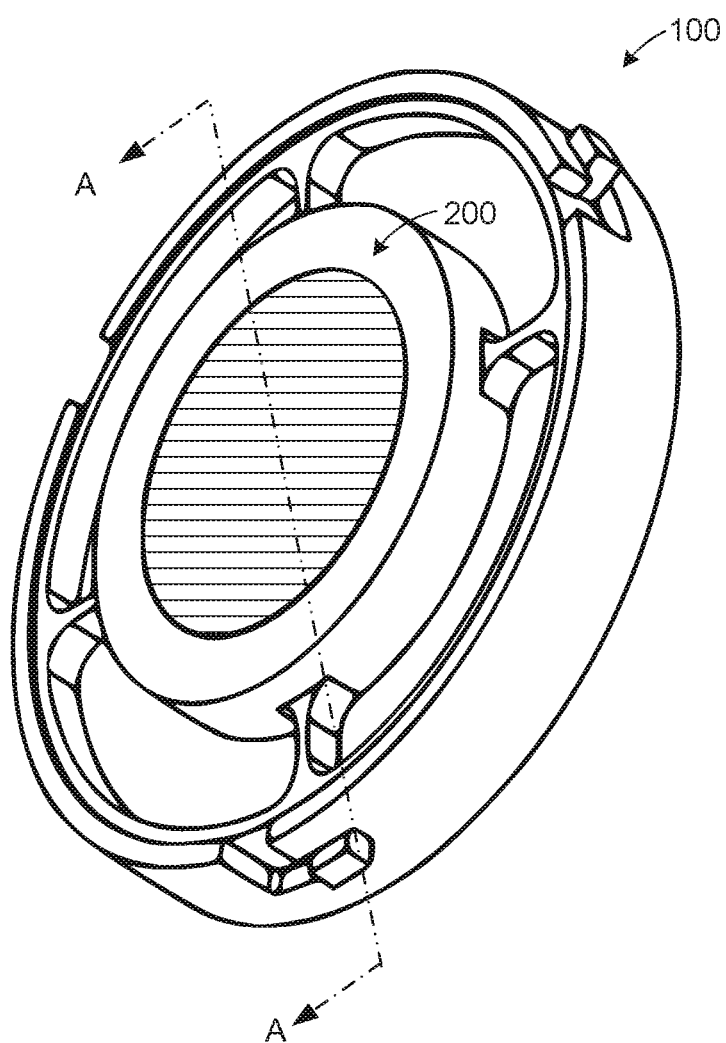
FIG. 1 illustrates a representative dark reference sample cup including an arrangement of materials for use as a dark reference standard according to various examples described herein.

The drawings illustrate only example embodiments and are therefore not to be considered limiting of the scope of the embodiments described herein, as other embodiments are within the scope of this disclosure. The elements and features shown in the drawings are not necessarily drawn to scale, emphasis instead being placed upon clearly illustrating the principles of the embodiments. Additionally, certain dimensions or positionings may be exaggerated to help visually convey certain principles. In the drawings, similar reference numerals between figures designate like or corresponding, but not necessarily the same, elements.

DETAILED DESCRIPTION

Spectrophotometry machines, known as spectrophotometers, measure the intensity of a light beam as a function of its wavelength. Some characteristics that differentiate spectrophotometers are spectral bandwidth, the percentage of sample-transmission, the logarithmic range of sample-absorption, and the percentage of reflectance measurement. Spectrophotometers are often used for transmittance and/or reflectance measurements on solutions, transparent or opaque solid materials, and gases over a range of electromagnetic radiation. The range of electromagnetic radiation can include ultra-violet (UV), visible (VIS), near-infrared (NIR), and infrared (IR) wavelengths. Over those ranges, spectrophotometers may need to be calibrated using reference standards to provide a suitable level of accuracy in measurements. A spectrophotometer may need to be calibrated using a combination of two or more different reference standards depending on the wavelength(s) of photometric evaluation and the absorbance characteristics of the reference standards over those wavelengths or ranges.

A spectrophotometer can use a monochromator containing a diffraction grating, for example, to generate a relatively wide spectrum of electromagnetic radiation across wavelengths, provided in relatively narrow ranges as the diffraction grating is scanned stepwise. The spectrum of electromagnetic radiation, in the relatively narrow ranges, can be applied to or directed toward a sample contained in a sample cup, for example, for analysis. A photodetector, such as a photomultiplier tube or photodiode, or an array of detectors, such as charge coupled devices (CCD) or photodiode arrays (PDA), can be used to detect observed wavelengths of transmittance and reflectance for the sample as the diffraction grating is scanned stepwise.

For transmittance measurements, a spectrophotometer measures a fraction of light that passes through, or is reflected from, a reference standard and a fraction of light that that passes through, or is reflected from, a sample under test. The spectrophotometer then quantitatively compares the intensities of the two measurements and computes a percentage of transmission, or reflection, for the sample as compared to the reference standard. For reflectance measurements, the spectrophotometer quantitatively compares the fraction of light which reflects from the reference standard and the fraction of light which reflects from the sample under test. Particularly, the irradiance photon density (e.g., in units of $W/m^2$) of transmitted and reflected light is measured with a photodetector as described above. The transmittance or reflectance value for each wavelength of the sample is then compared with the transmission or reflection values from the reference sample. A spectrophotometer can apply a logarithmic function to the linear transmittance, or reflectance, ratio to calculate absorbency of the sample.

In many types of spectrophotometers and other related instruments, the reflectance of a dark reference standard is set as a baseline value against which the reflectance of other samples are compared. Thus, the accuracy in measurements using spectrophotometers and other related instruments can depend in part on the quality of the dark reference standard. An ideal dark reference standard would uniformly reflect zero light (i.e., have 0% reflectivity or 100% absorbtion) across the spectral range of measurement for the instrument.

According to aspects of the embodiments described herein, a dark reference reflectance standard is embodied from an arrangement or composition of materials. The dark reference standard can be incorporated into a standard sample presentation cup used for powdered or slurry samples, for example, for ease of use. The dark reference reflectance standard offers a minimal amount of reflectivity across the spectrum of measurement and less than a desired specification of about 0.06% of incident energy reflected back to the instrument detection electronics (e.g., back to the photodetector). This refers to a reflection/reflectance of less than about 0.06% (i.e., R<0.06%, with a corresponding absorbance value of more than 3.22 Au).

The significantly low reflectance values for the dark reference standard embodiments described herein are sufficient to calibrate various types of dispersive-based instruments for dark current measurements used to establish measurement spectra. One advantage of the embodiments is that they provide measurement of dark current in the manner that normal reference standards and samples are measured. Such precise replication in measurement modality provides a more accurate dark correction than other common methods, such as using light traps and/or dark rooms. For certification purposes, the dark reference standards can be corrected to an absolute black standard by a comparison method with an absolute black factory light trap or measurements within a specially prepared dark room, for example.

In one embodiment, the dark reference standard includes a standard sample cup including an arrangement of materials that absorb light across the VIS-IR ranges (e.g., from about 350 nm to 2799 nm) to provide a dark standard measurement, and can be applied to other wavelength regions of the electromagnetic spectrum. The use of the standard sample cup has the advantage that the dark reflectance reference can be used in the standard instrument configuration. In other words, that means that the standard sample measurement apparatus may be installed during calibration. The old solution (e.g., using light traps) required the removal of the standard sample measurement apparatus during use for dark measurement.

One advantage to using an actual dark reference standard rather than a closed shutter or lamp shut-off is found in the ideal matched conditions when subsequently using a standard in the same (or similar style) sample cup used for samples. When not using a shutter or lamp shutoff, the stray reflections within the instrument are measured and therefore are cancelled in the calibration process.

Also, the electronic configuration of the instrument can be nearly identical when testing the dark reference standard as compared to general measurement conditions. This provides a precise dark record for computing spectra rather than an approximate record using other techniques. The dark reference standard can be measured each time the instrument is calibrated or aligned or at any other suitable time. To compute a test sample spectrum, a measurement of the sample, a white reference (or near 100 percent reflector), and a measurement of the dark standard can be used.

The general use of the dark reference standard embodiments described herein for computing a spectrum measured by a spectrophotometer is also described below. As in other forms of electronic and molecular spectroscopy, absorbance spectra are recorded using ratioed spectral data. This ratioed data consists of the sample spectrum, the reference spectrum, and the dark signal spectrum. The use of Beer's law for spectroscopic measurements is provided below.

To convert the light transmitted (or reflected) from a sample (I) ratioed to the incident energy ($I_o$) to Absorbance (A), as a linear estimate of spectral response to concentration, the equations provided below can be used. If only an internal reference is used for spectral collection, then the absorbance spectrum with respect to wavelength is computed as:

$$A = \log_{10}\left(\frac{I_0}{I}\right) = \log_{10}\left(\frac{1}{T}\right) = \log_{10}\left[\left(\frac{R_I - D_{R_I}}{S - D_S}\right)\right] \quad (1)$$

If an external standard material is used to calibrate the internal reference material, then the absorbance spectrum with respect to wavelength is computed as:

$$A = \log_{10}\left(\frac{I_0}{I}\right) = \log_{10}\left[\left(\frac{R_I + R_\Delta - D_{R_I}}{S - D_S}\right)\right], \text{ where} \quad (2)$$

$$R_\Delta = \frac{(R_E - D_{RE})}{(R_I - D_{RI})} \quad (3)$$

and S is the sample measurement; Ds is the Dark apparatus measurement for the Sample; $R_I$ is the internal Reference Measurement; $D_{RI}$ is the Dark apparatus measurement for the Internal Reference Sample; $R_E$ is the measurement of the external standard white reference material for calibration; $D_{RE}$ is the Dark apparatus measurement for the external standard reference material; and $R_A$ is the correction factor between the dark corrected $R_E$ and $R_I$.

The ideal dark apparatus measurement is a measurement where no energy from the source reflects back to the detector. The dark measurement represents the dark current changes in the instrument that are related to electronic noise and the stray reflections within the instrument. Such electronic noise in the instrument can be attributed to undesired noise present in the detection electronics, computational electronics, and control electronics even with little to no imputed energy reaching the detector.

The dark reference standard embodiments described herein provide a portable "light trap" that functions as a field-usable dark reflectance standard that is improved as compared to large, bulky manufacturing "light traps." Such dark reference standards can be used in conjunction with other certified reference materials for calibrating spectrophotometers and related instruments.

Turning to the drawings, FIG. 1 illustrates a representative dark reference sample cup 100 including an arrangement of materials 200 for use as a dark reference standard according to various examples described herein. As shown, the arrangement of materials 200 is secured in the center of the dark reference sample cup 100. Among the embodiments, any suitable type of sample cup similar to the dark reference sample cup 100 can be used to secure and hold the arrangement of materials 200 for the dark reference standard. For example, depending upon the type and style of the measuring instrument, various types and sizes of sample cups can be used.

Using the dark reference sample cup 100 rather than a closed shutter or lamp shut-off permits a more representative dark reference standard condition measurement for comparison with measurements taken using the same sample cup used for samples. Also, the electronic configuration of the instrument can be nearly identical when testing the dark reference standard as compared to general measurement conditions. When not using a shutter or lamp shutoff, the stray reflections within the instrument are measured and cancelled out during the calibration process using the previously described equations. This provides a precise dark record for computing spectra rather than an approximate record using other techniques.

The dark reference sample cup 100 shown in FIG. 1 is provided by way of representative example. The embodiments are not limited to dark reference samples having the form or shape of the dark reference sample cup 100 shown in FIG. 1. Instead, the embodiments can vary in shape and/or size as compared to that shown.

Figure 2:
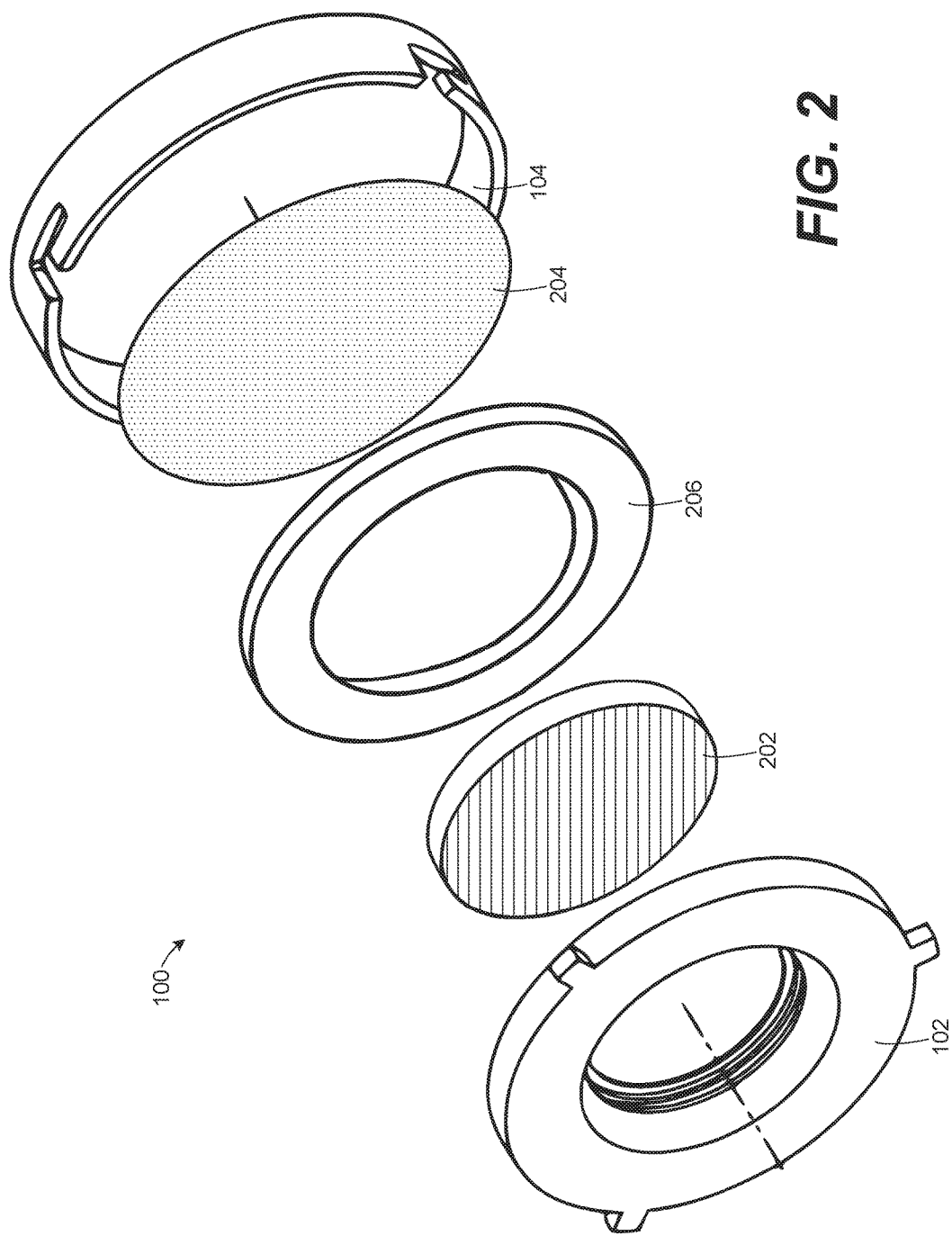
FIG. 2 illustrates an exploded view of the sample cup shown in FIG. 1 according to various examples described herein.

FIG. 2 illustrates an exploded view of the dark reference sample cup 100 shown in FIG. 1. As shown, the dark reference sample cup 100 includes the front sample cup housing section 102 and the back sample cup housing section 104. The dark reference sample cup 100 also includes a dark glass 202 and black polymer film 204, which are representative of the arrangement of materials 200 shown in FIG. 1, and an annular spacer 206. When the dark reference sample cup 100 is assembled, the dark glass 202 is surrounded and centrally positioned by the annular spacer 206. Further, the dark glass 202, the black polymer film 204, and the annular spacer 206 are secured between the front sample cup housing section 102 and the back sample cup housing section 104.

In one embodiment, the dark glass 202 can comprise a suitable type of welding glass, such as Sellstrom® 16510 shade ten (10) welding glass, US Forge® shade twelve (12) glass, or a similar type of tinted glass, plastic, or other constant- or consistent-density dark filter made formed as one or more lenses. The dark glass 202 can vary in thickness from about 2 mm or less to about 5 mm or more among embodiments, but the embodiments are not particularly limited to any thickness of the dark glass 202.

The black polymer film 204 can comprise a suitable dark absorbing material, such as a polymer film formed or impregnated with one or more carbon black and/or carbon black masterbatch materials or dyes. In one embodiment, the black polymer film 204 can be embodied as a polyethylene "garbage bag" material having a thickness ranging from about 0.5 mil to about 6 mil. In another embodiment, the black polymer film 204 can be embodied as polyoxymethylene, also known as acetal, polyacetal, and polyformaldehyde (e.g., DuPont™ Delrin), impregnated with one or more carbon black and/or carbon black masterbatch materials or dyes. The black polymer film 204 can be selected for low spectral signature such that it uniformly absorbs light across the spectral range of instrument measurement. In other aspects, a light absorbing polymer film, a dark backing material, or an opaque backing material that absorbs light energy for the wavelengths of interest can also be used to prevent light leakage from the back and front reflection from the front.

When inserted for testing into an instrument, the dark glass 202 of the dark reference sample cup 100 may be positioned higher than a normal sample height by about 8 mm. However, using the same type of cup as would be used to hold a sample under test makes measurements comparable and maintains matched conditions. This is important for true correction of the measurement for typical samples. This variation in space between the dark glass 202 and the detector of the instrument can reduce the amount of light reflected back into the detectors.

Figure 3:
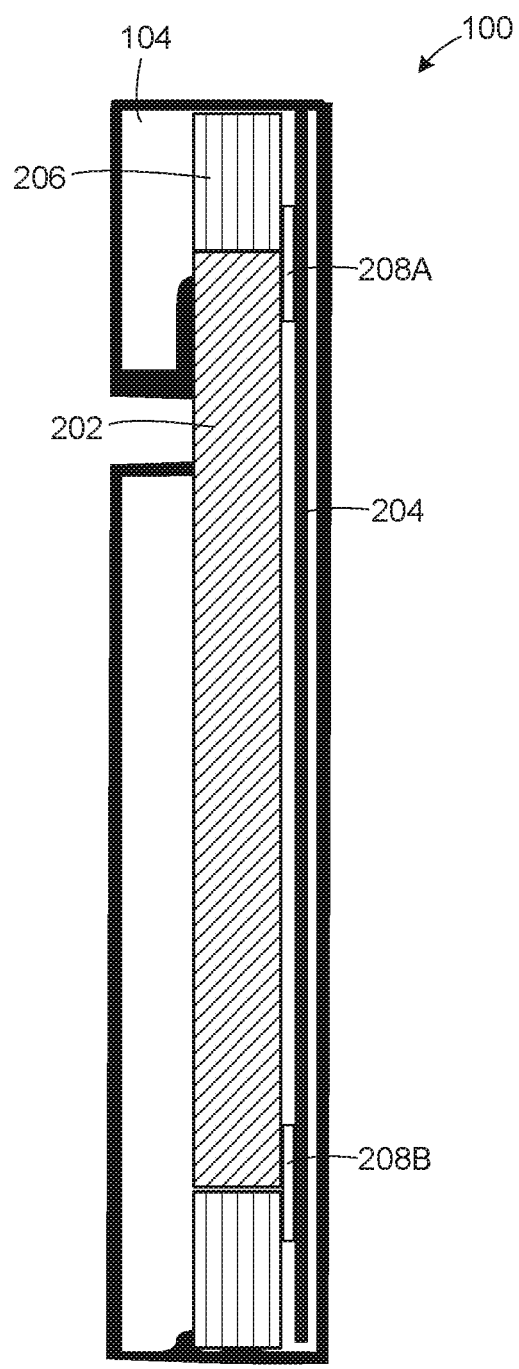
FIG. 3 illustrates the cross-sectional view "A-A" of the arrangement of the dark reference sample cup designated in FIG. 1 according to various examples described herein.

FIG. 3 illustrates the cross-sectional view "A-A" of the arrangement of the dark reference sample cup 100 designated in FIG. 1. As shown in the side view, the dark glass 202 and the black polymer film 204 can be placed in a side-by-side arrangement. The black polymer film 204 is cut to substantially cover the inner surface of the back sample cup housing section 104. The dark glass 202 is surrounded and centrally positioned by the annular spacer 206 within the back sample cup housing section 104.

In some embodiments, one or more spacers 208A, 208B of suitable thickness can be positioned between the dark glass 202 and the black polymer film 204. Any suitable number and arrangement of the spacers 208A, 208B can be positioned between the dark glass 202 and the black polymer film 204. As shown in FIG. 3, the spacers 208A, 208B are positioned to overlap certain portions of the annular interface between the dark glass 202 and the annular spacer 206.

The spacers 208A, 208B can be embodied as foam, plastic, paper, or other suitable materials. When the dark reference sample cup 100 is assembled, the spacers 208A, 208B can be compressed (e.g., foam is used for the spacers 208A, 208B), act as compression "springs," and keep the dark glass 202 and the black polymer film 204 from shifting. The spacers 208A, 208B can also be relied upon to create a relatively small space between the dark glass 202 and the black polymer film 204 when the dark reference sample cup 100 is assembled. In some embodiments, however, the dark glass 202 and the black polymer film 204 can be arranged to press against each other and the spacers 208A, 208B can be omitted. The spacers 208A, 208B can be held in place by compression and/or with or without using adhesive.

Figure 4:
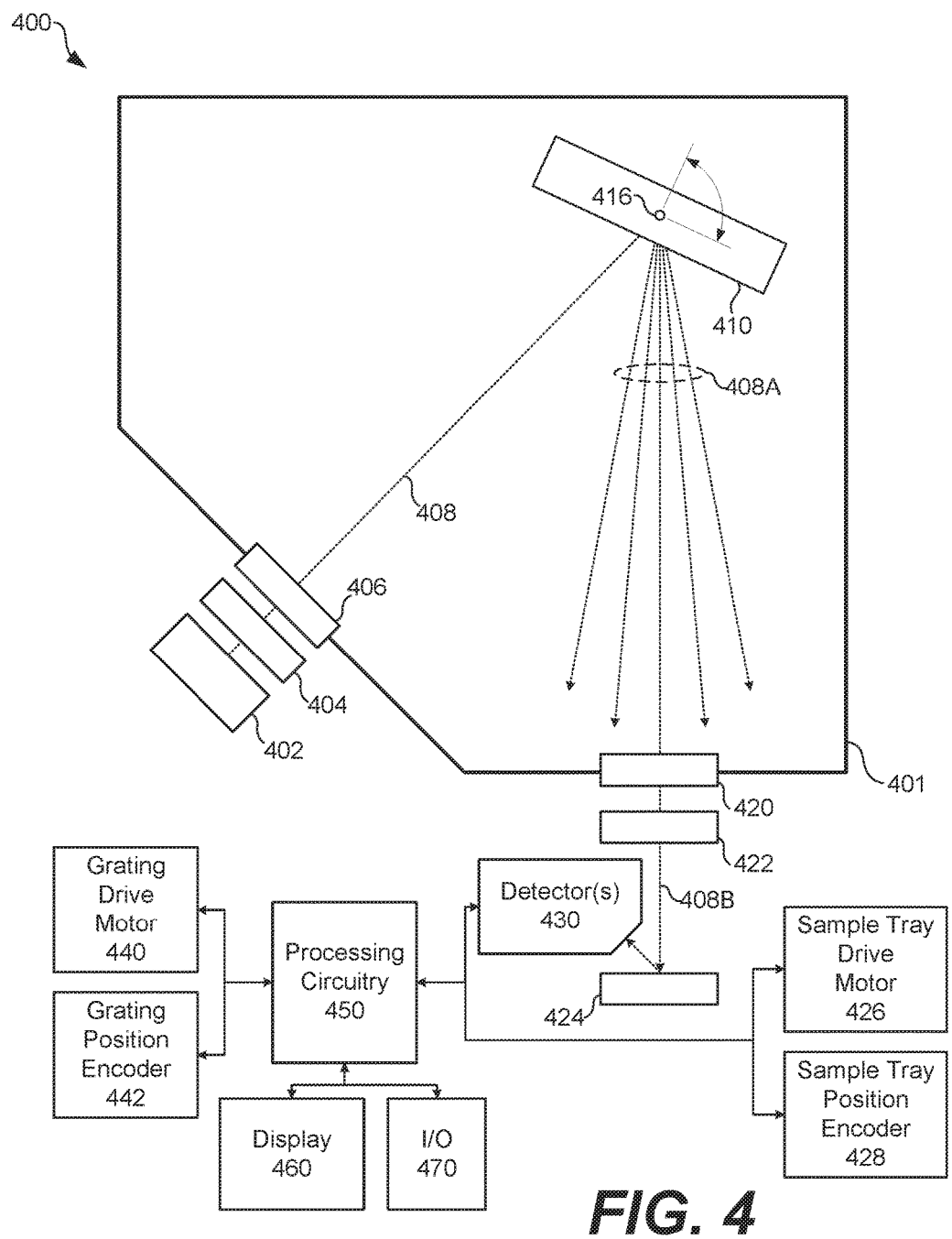
FIG. 4 illustrates an example monochromator for taking measurements according to an embodiment described herein.

FIG. 4 illustrates an example monochromator 400 for taking dark reference standard measurements using the dark reference sample cup 100 shown in FIG. 1. The monochromator 400 is presented as one example of a spectrophotometric instrument that can used to measure a dark reference standard according to the embodiments described herein. The embodiments are not limited to use with monochromators, however, or any other particular types of measurement instruments.

As illustrated, the monochromator 400 includes an enclosure 401 for a diffraction grating 410, a light source assembly 402, an entrance optics assembly 404, an entrance slit assembly 406, an exit slit assembly 420, an exit optics assembly 422, a sample tray 424, a sample tray drive motor 426, a sample tray position encoder 428, a detector 430, a grating drive motor 440, a grating position encoder 442, processing circuitry 450, a display 460, and input/output (I/O) interfaces 470.

In one embodiment, the light source assembly 402 includes a halogen light bulb to generate broadband light 408, although any source of broadband light suitable for the application can be relied upon among embodiments. The entrance optics assembly 404 can include optical elements that collimate the broadband light, such as one or more spaced-apart expander and/or plano-convex lenses or other elements, without limitation. The entrance slit assembly 406 includes a slit though which at least a portion of the broadband light 408 can be selectively passed into the enclosure 401.

Conventionally, the entrance slit of the monochromator 400 could be selectively covered and/or uncovered by a sliding shutter (not shown) driven by an offset solenoid (not shown) to block the broadband light 408 from entering the enclosure 401. Any suitable shutter mechanism can be used for this purpose. In that case, the shuttering operation of the solenoid can be controlled by the processing circuitry 450 to block the broadband light 408 (or reflections or dispersions thereof) from reaching the detector 430 during certain operations of the monochromator 400, such as dark scan, calibration (or reference) scan, and live scan operations. As described herein, dark scans, calibration scans, and live scan operations can be performed using the monochromator 400 without the need to cover the entrance slit of the monochromator 400 or to block the broadband light 408 when using the dark reference sample cup 100 shown in FIG. 1.

In one embodiment, the diffraction grating 410 cab include an ultra-violet (UV) to visible (VIS) grating, a near-infrared (NIR) to infrared (IR) grating, or other grating to disperse the broadband light 408 other (e.g., wider or narrower) ranges of wavelengths. The diffraction grating 410 can be embodied as one or more substrates of various sizes with parallel grooves replicated on their surfaces, as would be appreciated in the art. The diffraction grating 410 disperses the broadband light 408 by spatially separating it according to wavelength, resulting in diffracted, dispersed wavelengths of light 408A. Various methods of manufacture of diffraction gratings are known in the field, and the diffraction gratings described herein can be manufactured using any known method, such as by replication from master gratings, interferometric control, holographic generation, ion etching, or lithography, for example. Diffraction gratings can also include a coating of reflective material over the grooves, to reflect light.

The diffraction grating 410 can be selected for use over any desired range of wavelengths and sourced from any manufacturer of diffraction gratings, such as Optometrics Corporation of Littleton, Mass., Grating Works of Acton, Mass., or Richardson Gratings™ of Rochester, N.Y., for example and without limitation. One example of a diffraction grating for use with near IR wavelengths is a Hitachi Holographic Grating with a groove density of about 600 grooves per mm, although it should be appreciated that the use of other diffraction gratings is within the scope and spirit of the embodiments.

Certain diffraction gratings have specific, blazed efficiency curves. The choice of an optimal efficiency curve for a grating depends on the specific application. In the context of a monochromator, linear efficiency is usually desired. In other words, the intensity of the diffracted bands of light should be constant across the spectral range of light being dispersed. It is noted, however, that the efficiency (e.g., the power or intensity of monochromatic light diffracted relative to the intensity of the incident light) and linearity of a diffraction grating is generally not constant as the angle of incident light upon the grating is varied. In other words, as a diffraction grating is rotated in the presence of incident light upon its surface, the intensity and/or linearity of the diffracted bands of light may not be perfectly uniform or linear.

To provide the diffracted, dispersed wavelengths of light 408A, the diffraction grating 410 is mounted to rotate about a pivot point 416 by way of the grating drive motor 440. Among other functions, the processing circuitry 450 can control the grating drive motor 440 to rotate the diffraction grating 410 about the pivot point 416 in the presence of the broadband light 408. More particularly, the processing circuitry 450 can control the grating drive motor 440 to control the rate of angular velocity or displacement of the diffraction grating 410 in the presence of the broadband light 408.

Further, the processing circuitry 450 can control the grating drive motor 440 to regulate an angular velocity of the diffraction grating 410 based on an angular orientation of the diffraction grating 410.

After being reflected from the diffraction grating 410, the exit slit assembly 420 can pass a portion 408B of the dispersed wavelengths of light 408A out from the enclosure 401. The exit slit assembly 420 can include a physical slit in the enclosure 401 through which the portion 408B of light can pass. The exit optics assembly 422 includes optical elements that collect the portion 408B of light, such as one or more plano-convex collection lenses, for example, without limitation. In some embodiments, the exit optics assembly 422 can also include one or more 45° mirrors, etc., to further direct the portion 408B of light within the monochromator 400.

After being collected and/or directed by the exit optics assembly 422, the portion 408B of the dispersed wavelengths of light 408A falls incident upon the sample tray 424 and/or a sample for evaluation in or on the sample tray 424. In turn, the portion 408B of light is reflected off the sample and captured by the detector 430. In one embodiment, the detector 430 is positioned proximate to the sample tray 424 and measures the intensity of the light reflected from the sample or the fraction of radiation absorbed by the sample at specific wavelengths (i.e., the absorbance of the sample).

The detector 430 can be embodied as a silicon-based multichannel array CCD or PDA detector of relatively high grade for suitable sensitivity, uniformity, and noise characteristics and may be tailored for use with the UV-VIS, the NIR-IR range, or other ranges of wavelengths of light. The detector 430 converts the first portion of reflected light to an electrical signal for conversion to data values from which a quantitative analysis of a variety of characteristics of the sample, including constituent analysis, moisture content, taste, texture, viscosity, etc., can be determined.

The detector 430 can include one or more lensed assemblies including one or more image or light sensors that observe the reflection of light from the sample at a point of illumination. The field of view of the detector 430 can be restricted and the relative geometry and/or placement of the lensed assemblies can be selected to maximize energy collection while minimizing stray light inclusion. Further details regarding the geometry of the detector 430 and the sample tray 424 are described below with reference to FIGS. 5A-5C.

The grating drive motor 140 rotates the diffraction grating 410 about the pivot point 116. As described above, the processing circuitry 150 controls the position, rate of angular velocity, and/or acceleration of the diffraction grating 410 by way of the grating drive motor 440. Among embodiments, the grating drive motor 440 can be embodied as any suitable permanent magnet stepper motor that directly drives the rotation of the diffraction grating 410, although other types of motors can be used. For example, variable reluctance motors, brushless DC motors, hybrid stepper motors, or servo motors can be relied upon. Preferably, the grating drive motor 440 is selected to provide a continuous or nearly continuous range of angular displacement with good response to control by the processing circuitry 450.

The grating position encoder 442 provides feedback on the angular orientation of the diffraction grating 410. For example, the grating position encoder 442 can provide an encoded signal representative of the absolute angular orientation or position of the diffraction grating 410. This position information is provided to the processing circuitry 450 as feedback for control of the grating drive motor 440. In one embodiment, the grating position encoder 442 can be selected from among any suitable rotary position encoder having high enough resolution in rotary position for the application. In one embodiment, an encoder can be selected to yield a 1 in 25,600 increment of rotation, representative of 0.1 nm of dispersed monochromatic light for certain diffraction gratings. The position or increment of rotation can be interpolated in some embodiments for even greater resolution of rotary position. One example of such a rotary position encoder is the HEIDENHAIN ERN 480 encoder unit, although other types of encoders can be relied upon among embodiments.

In one embodiment, the sample tray drive motor 426 rotates the sample tray 424 about a pivot point. The processing circuitry 450 controls an angle of incidence of the portion 408B of light upon the sample tray 424 and/or a sample in or on the sample tray 424. The sample tray position encoder 428 provides feedback on the angular orientation of the sample tray 424 to the processing circuitry 450. The angular orientation information from the sample tray position encoder 428 is provided to the processing circuitry 450 as feedback for control of the sample tray drive motor 426. In one aspect, the processing circuitry 450 controls the sample tray drive motor 426 to adjust an angle of incidence of the portion 408B of light upon the sample tray 424, depending upon the type of measurement being taken by the monochromator 400. Further details regarding control of the angle of incidence of the portion 408B of light upon the sample tray 424 are described below with reference to FIGS. 5A-5C.

The processing circuitry 450 can be embodied as one or more circuits, processors, processing circuits, or any combination thereof, including memory, that monitors and controls the elements of the monochromator 400. In this context, the processing circuitry 450 can be configured to capture, store, and analyze signals and/or data provided by the detector 430, forward and/or display captured data to another computing device or the display 460, receive control feedback from a user operating the I/O interfaces 470, and store and process various types of data. The processing circuitry 450 can also be configured to perform the necessary calculations and output control signals to elements of the monochromator 400, so as to implement the process described below with reference to FIG. 6. Further, the processing circuitry 450 can also include driver circuitry for powering and/or driving the grating drive motor 440 and the sample tray drive motor 426, among other elements which are under computer control.

For context, a brief overview of the operation of the monochromator 400 is described. In operation, the light source of the light source assembly 402 emits, in the broadband light 408, a relatively broad spectrum of light or radiation. The entrance optics assembly 404 collimates the broadband light 408, and at least a portion of the broadband light is then projected through an entrance slit of the entrance slit assembly 406 and onto the diffraction grating 410. The diffraction grating 410 provides (i.e., reflects) dispersed wavelengths of light 408A by diffraction of the portion of the broadband light 408 incident upon it. The diffraction grating 410 is positioned and rotated over time by the grating drive motor 440 so that the portion 408B of the first dispersed wavelengths of light 408A, which varies or scans over time, passes through an exit slit of the exit slit assembly 420, while the exit slit assembly 420 blocks other wavelengths of the light 408A from exiting the enclosure 401.

The portion 408B of the light 408A that passes through the exit slit assembly 420 is determined by the angle of the diffraction grating 410, and a spectrum of UV-VIS, NIR-IR, or other spectral range of light is scanned by rotation of the diffraction grating 410 by the grating drive motor 440. The portion 408B of the light 408A that passes through the exit slit assembly 420 is collected by the exit optics assembly 422 and directed incident onto a sample in the sample tray 424. The detector 430, which is situated proximate to the sample tray 424, measures the intensity of diffused, reflected light from the sample and converts the power of the reflected light into an electrical signal and/or data values. Using the electrical signal and/or data values, a quantitative analysis of the characteristics of the sample, such as sample constituents, moisture content, taste, texture, viscosity, etc., can be quantitatively determined.

Turning to FIGS. 5A-5C, FIG. 5A illustrates an example geometry of the detector 430 and the sampling tray 424 in a measurement tract of the monochromator 400 of FIG. 4, FIG. 5B illustrates a second example of the geometry of the detector 430 and the sampling tray 424 in the measurement tract, and FIG. 5C illustrates a third example of the geometry of the detector 430 and the sampling tray 424 in the measurement tract. The measurement tracts shown in FIGS. 5A-5C are representative and provided by way of example as other arrangements of detectors, sampling trays, mirrors, etc., can be used in other instruments. As described in further detail below, the dark reference sample cup 100 (or a similar dark reference sample according to the embodiments) can be placed or introduced into the measurement tracts shown in FIGS. 5A-5C to absorb light generated by the light source assembly 402 of the monochromator 400. In that way, the light will not be detected by the detector 430, and a dark reference standard measurement can be taken.

The example geometry of the detector 430 and sampling tray 424 in FIG. 5A can be identified as a 0°/45° geometry, the example geometry of the detector 430 and sampling tray 424 in FIG. 5B can identified as a 45°/0° geometry, and the example geometry of the detector 430 and sampling tray 424 in FIG. 5C can identified as a 22.5°/22.5° geometry. These geometries are defined with reference to the angular difference between the incidence of light upon the sampling tray 424 as compared to the normal "N" of the sampling tray 424, and the angular difference between the normal "N" of the sampling tray 424 and the direction of light reflected into the detector 430. Again, the geometries shown in FIGS. 5A-5C are representative and others are within the scope of the embodiments.

For dark reference standard measurements, an individual can introduce and secure the dark reference sample cup 100 (or a similar dark reference sample according to the embodiments) into the measurement tract of the monochromator 400. For example, the dark reference sample cup 100 can be introduced upon and potentially secured to the sampling tray 424. In some cases, the monochromator 400 can rotate the angle of the sampling tray 424, including the dark reference sample cup 100, to vary the geometry between the dark reference sample cup 100 and the detector 430. Thus, to the extent that the angle of incidence of light on a sample impacts the result of a dark reference standard measurement taken by the monochromator 400, the processing circuitry 450 can rotate the angular orientation of the sample tray 424 and the dark reference sample cup 100 by control of the sample tray drive motor 426. Further, the processing circuitry 450 can determine a relative or absolute angular orientation of the sampling tray 424 and the dark reference sample cup 100 based on feedback from the sample tray position encoder 428.

Figure 6:
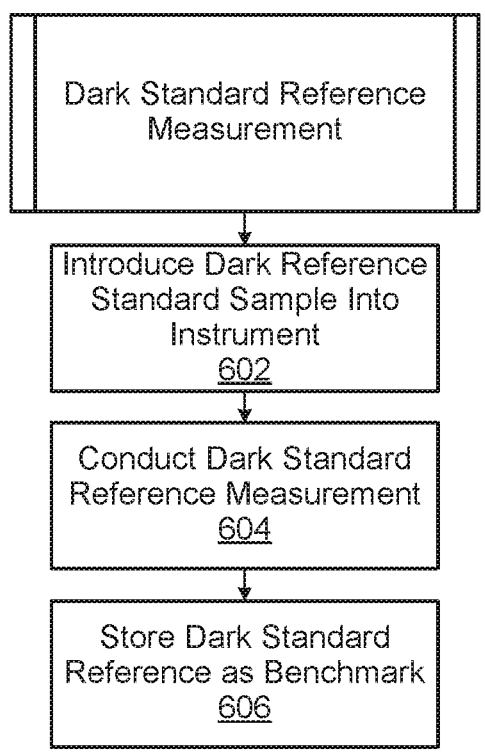
FIG. 6 illustrates an example process or method of dark reference standard measurement according to an embodiment described herein.

FIG. 6 illustrates an example process or method of dark reference standard measurement according to an embodiment described herein. The flowchart shown in FIG. 6 can be viewed as example steps performed by the monochromator 400 of FIG. 4 to perform a dark reference standard measurement. Although not explicitly described in all steps, the processing circuitry 150 can direct one or more components of the monochromator 400 to perform one or more steps illustrated in FIG. 6. However, other monochromators or instruments similar to the monochromator 400 can perform the process.

At step 602, the process includes introducing a dark reference standard sample into a measurement tract of a spectrophotometric instrument. For example, the dark reference sample cup 100 can be introduced to the measurement tract of the monochromator 400. The dark reference sample cup 100 can be introduced manually by an individual or in an automated fashion using a sample wheel, for example, driven by motors, servos, or other means. As one example, the dark reference sample cup 100 can be placed upon and, in some cases, secured to the sample tray 424.

At step 604, the process includes conducting a dark reference standard measurement. For example, the monochromator 400 can illuminate the light source of the light source assembly 402 to emit the broadband light 408. In turn, the diffraction grating 410 provides (i.e., reflects) dispersed wavelengths of light 408A by diffraction of the portion of the broadband light 408 incident upon it. The diffraction grating 410 can be rotated over time by the grating drive motor 440 so that the portion 408B of the first dispersed wavelengths of light 408A scans over time through an exit slit of the exit slit assembly 420.

The portion 408B of the light 408A that passes through the exit slit assembly 420 is determined by the angle of the diffraction grating 410, and a spectrum of UV-VIS, NIR-IR, or other spectral range of light is scanned by rotation of the diffraction grating 410 by the grating drive motor 440. The portion 408B of the light 408A that passes through the exit slit assembly 420 is collected by the exit optics assembly 422 and directed incident onto the dark reference sample cup 100 on the sample tray 424.

At the same time, the detector 430, which can be situated as shown in any of the examples of FIGS. 5A-5C (or other arrangement), detects light (to the extent there is any) in the measurement tract of the monochromator 400. The detector 430 converts the power of any light in the measurement tract into an electrical signal and/or data values to generate a dark reference standard for the monochromator 400. The detector 430 can detect any light in the measurement tract over the UV-VIS, NIR-IR, or other spectral range while light is scanned by rotation of the diffraction grating 410 by the grating drive motor 440.

At step 606, the process includes storing the dark reference standard measured at step 604 in the memory of the processing circuitry 450. Once stored in memory, the measured dark reference standard can be used as a baseline value against which the reflectance of other sample measurements taken by the monochromator 400 can be compared.

In some cases, the performance of each dark reference sample cup 100 that is manufactured can be measured after it is assembled using a master calibrated instrument. Further, each dark reference sample cup 100 that is manufactured can be marked with a unique serial number and associated with its own dark reference standard data, as measured by the master calibrated instrument. Thus, to the extent that the absorbance of each manufactured dark reference sample cup 100 varies as compared to each other, each can be associated with a certain performance in absorbance over a range of wavelengths.

When any given dark reference sample cup 100 is calibrated and then used with another instrument, its own dark reference standard data (i.e., as measured by the master calibrated instrument) can be loaded into the memory of the instrument for comparison and/or correction of measurement data. Further, for certification purposes, any given dark reference sample cup 100 can be corrected to an absolute black standard by comparison with an absolute black factory light trap or measurements within a specially prepared dark room, for example.

The process shown in FIG. 6 can be performed when the monochromator 400 is in its standard instrument configuration. In other words, the dark reference sample cup 100 can be measured by the monochromator 400 without the installation and/or removal of a light trap, which takes time. Further, the process can be performed without darkening the entire room, which can be cumbersome and difficult for individuals in the room. Moreover, using the dark reference sample cup 100 rather than a closed shutter or lamp shut-off leads to ideal matched conditions when subsequently using a standard in the same (or similar style) sample cup used for samples. When not using a shutter or lamp shutoff, the stray reflections within the instrument are measured and can be cancelled in the calibration process.

As noted at the outset, accuracy in measurements using spectrophotometers and other related instruments can depend in part on the quality of the dark reference standard. An ideal dark reference standard would uniformly reflect zero light (i.e., have 0% reflectivity or 100% absorbtion) across the spectral range of measurement for the instrument.

Figure 7:
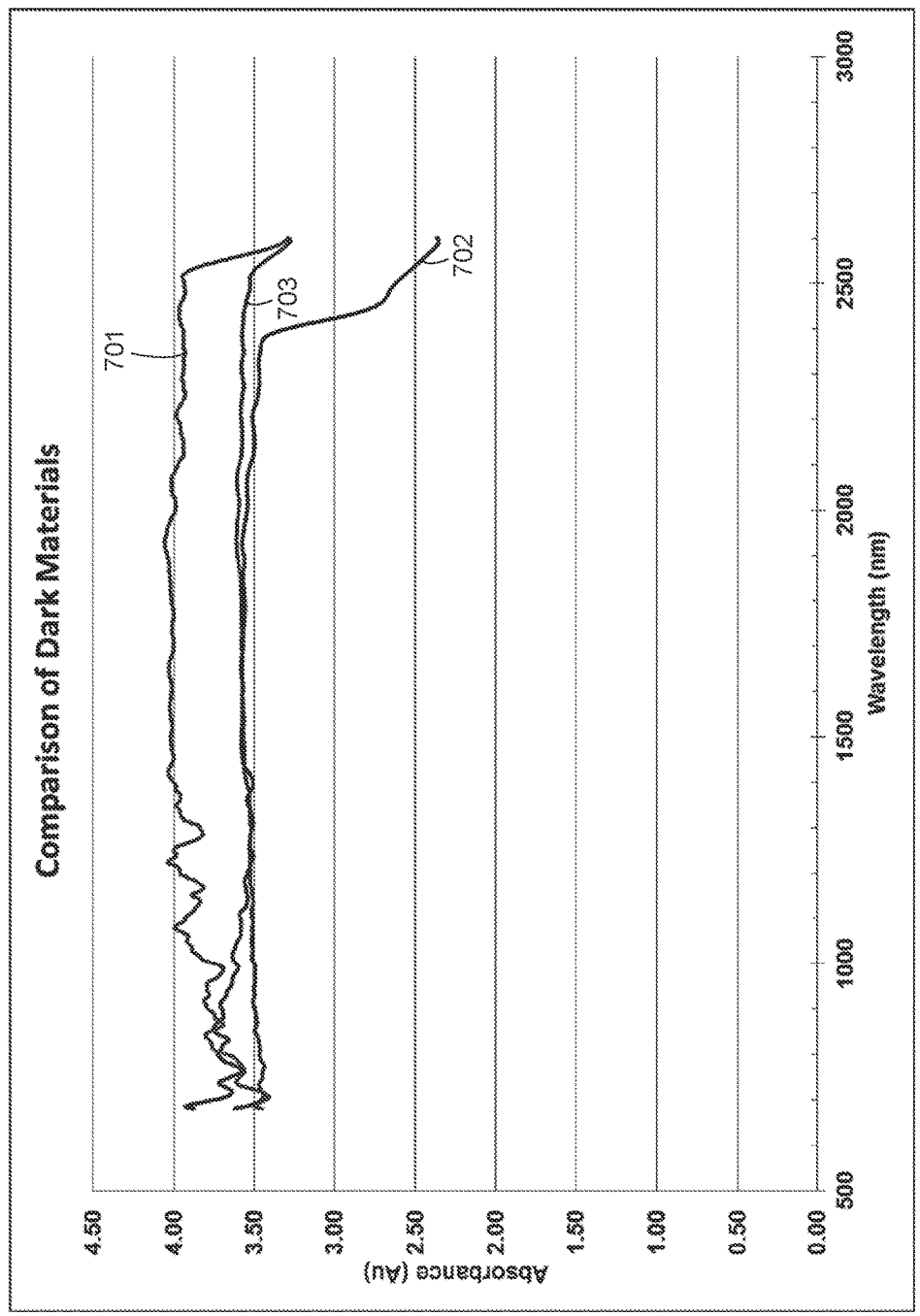
FIG. 7 illustrates a comparison of spectra obtained from an instrument using a dark room, light trap, and the dark reference standard materials described herein.

FIG. 7 illustrates a comparison of spectra obtained from an instrument using a completely dark room, light trap, and the dark reference standard materials described herein. Particularly, FIG. 7 illustrates the dark room spectra 701, light trap spectra 702, and the dark reference standard spectra 703. As shown, the dark reference standard spectra 403 exhibits a significantly flat response and relatively high absorbance from about 650 nanometers through at least 2500 nanometers. Thus, the dark reference standard materials described herein exhibit a minimal amount of reflectivity across the spectrum of measurement and less than a desired specification of about 0.06% of incident energy reflected back to the instrument detection electronics.

Table 1 shows a further comparison of three dark reference measurements shown in FIG. 7, including the dark reference standard according to the embodiments (i.e., Cert Stnd), the light trap, and the dark room. For correlation and r-squared (RSQ coefficient of determination), the various absorbance spectra of the dark reflectance measurement methods can be compared to a perfectly horizontal absorbance line across wavelengths of measurement.

TABLE 1

Dark Standard Method Statistical Parameter Comparison

| METHOD | CORR | RSQ | STDEV | SLOPE | AVE. ABS. |
|---|---|---|---|---|---|
| Cart Stnd | 0.034 | 0.001155 | 0.054 | 810.9 | 3.540 |
| Light Trap | 0.031 | 0.000951 | 0.299 | 4036.4 | 3.472 |
| Dark Rm | −0.068 | 0.004692 | 0.153 | −4589.5 | 3.908 |

An ideal dark reflectance standard would exhibit the highest correlation (and r-squared) to a straight horizontal line, the highest average absorbance above 3.1 Au, the lowest standard deviation (lowest variation and noise), and the lowest slope (most linear). With reference to Table 1, the dark reference standard according to the embodiments (Cert Stnd) surpasses the light trap in each of the parameters. The dark room has the highest overall average absorbance (lowest reflectivity), but demonstrates more noise and exhibits a large standard deviation.

For many applications, the region above 2500 nm in measurement wavelength is particularly important since spectrophotometer measurement accuracy for higher wavelengths requires a more accurate correction for the dark signal. This is because the energy is quite low in the higher wavelength regions due to lamp energy optical throughput and detector sensitivity. The average absorbance values above 2500 nm and above 2550 nm for the dark reference standard according to the embodiments as compared to a light trap and a dark room are shown in Table 2.

TABLE 2

Dark Standard Method Average Absorbance Comparison above 2500 nm and 2550 nm

| METHOD | AVE. ABS >2500 nm | AVE. ABS >2550 nm |
|---|---|---|
| Cert Stnd | 3.416 | 3.335 |
| Light Trap | 2.471 | 2.398 |
| Dark Rm | 3.665 | 3.449 |

Although embodiments have been described herein in detail, the descriptions are by way of example. The features of the embodiments described herein are representative and, in alternative embodiments, certain features and elements may be added or omitted. Additionally, modifications to aspects of the embodiments described herein may be made by those skilled in the art without departing from the spirit and scope of the present invention defined in the following claims, the scope of which are to be accorded the broadest interpretation so as to encompass modifications and equivalent structures.

At least the following is claimed:

1. A dark reference standard for a spectrophotometric instrument, comprising:
    a sample cup; and
    an arrangement of dark reference standard materials in the sample cup, the arrangement of dark reference standard materials comprising:
        a dark backing material covering an inner back surface of the sample cup; and
        a dark glass in a side-by-side arrangement over the dark backing material.

2. The dark reference standard according to claim 1, wherein the dark backing material comprises a polymer film.

3. The dark reference standard according to claim 2, wherein the polymer film is impregnated with at least one carbon black material or dye.

4. The dark reference standard according to claim 2, wherein the polymer film comprises a polyoxymethylene film impregnated with at least one carbon black material or dye.

5. The dark reference standard according to claim 1, wherein the dark glass comprises a welding glass.

6. The dark reference standard according to claim 1, wherein the dark glass comprises a shade ten or twelve welding glass.

7. The dark reference standard according to claim 1, wherein the dark reference standard further includes at least one spacer between the dark glass and the dark backing material in the sample cup.

8. The dark reference standard according to claim 1, wherein the dark reference standard further includes an annular spacer that surrounds and centrally positions the dark glass in the sample cup.

9. A dark reference standard for a spectrophotometric instrument, comprising:
    a sample cup; and
    an arrangement of dark reference standard materials, the arrangement of dark reference standard materials comprising:
        a polymer film impregnated with at least one carbon black material or dye covering an inner back surface of the sample cup; and
        a welding glass in a side-by-side arrangement over the polymer film.

10. The dark reference standard according to claim 9, wherein the welding glass comprises a shade ten or twelve welding glass.

11. The dark reference standard according to claim 9, wherein the dark reference standard further includes at least one spacer between the welding glass and the polymer film.

12. The dark reference standard according to claim 9, wherein the dark reference standard further includes an annular spacer that surrounds and centrally positions the welding glass in the sample cup.

13. A dark reference standard for a spectrophotometric instrument, comprising:
    a sample cup; and
    an arrangement of dark reference standard materials in the sample cup, the arrangement of dark reference standard materials comprising:
        a dark backing material covering an inner back surface of the sample cup; and
        a dark glass in a side-by-side arrangement over the dark backing material; and
    an annular spacer that surrounds and centrally positions the dark glass in the sample cup.

14. The dark reference standard according to claim 13, wherein the dark backing material comprises a polymer film.

15. The dark reference standard according to claim 14, wherein the polymer film is impregnated with at least one carbon black material or dye.

16. The dark reference standard according to claim 14, wherein the polymer film comprises a polyoxymethylene film impregnated with at least one carbon black material or dye.

17. The dark reference standard according to claim 13, wherein the dark glass comprises a welding glass.

18. The dark reference standard according to claim 13, wherein the dark glass comprises a shade ten or twelve welding glass.

19. The dark reference standard according to claim 13, wherein the dark reference standard further includes at least one spacer between the dark glass and the dark backing material in the sample cup.

* * * * *